United States Patent [19]

Watts, Jr.

[11] 4,088,700

[45] May 9, 1978

[54] PROCESS FOR THE HYDROGENOLYSIS OF DIOXOLANES

[75] Inventor: Lewis W. Watts, Jr., Austin, Tex.

[73] Assignee: Texaco Development Corporation, New York, N.Y.

[21] Appl. No.: 727,078

[22] Filed: Sep. 27, 1976

[51] Int. Cl.$^2$ ............................................. C07C 41/00
[52] U.S. Cl. .......................... 260/611 R; 260/611 A; 260/615 R; 260/614 R; 260/612 D; 568/865; 568/835; 568/799; 568/700
[58] Field of Search ........... 260/632 B, 615 R, 611 A, 260/611 R

[56] References Cited

U.S. PATENT DOCUMENTS

| | | | |
|---|---|---|---|
| 3,170,958 | 2/1965 | Howard | 260/615 R X |
| 3,277,187 | 10/1966 | Dewhirst | 260/615 R X |

*Primary Examiner*—Bernard Helfin
*Attorney, Agent, or Firm*—Carl G. Ries; Thomas H. Whaley; Walter D. Hunter

[57] ABSTRACT

An improved process for the hydrogenolysis of acetals and ketals of organic hydrocarbons is described. The improvement resides in using a catalyst system including a halide of a Group III A element and a supported platinum or rhodium hydrogenation catalyst or combination thereof, thus enabling the process to be practiced at a temperature of from about −15° C. to about 125° C. and a pressure of from about 50 psia to about 2000 psia. The preferred Group III A halides are boron trifluoride and aluminum trichloride.

13 Claims, No Drawings

PROCESS FOR THE HYDROGENOLYSIS OF DIOXOLANES

BACKGROUND OF THE INVENTION

1. Field of the Invention

The invention pertains to an improved process for the hydrogenolysis of acetals and ketals of organic hydrocarbons by utilizing a new catalyst system.

2. Description of the Prior Art

Hydrogenolysis of acetals and ketals of organic hydrocarbons has heretofore been accomplished by employing stoichiometric amounts of either halo-alkyl aluminum compounds or mixtures of aluminum halides and lithium aluminum hydride. The extremely flammable nature of these reagents is well-known. The $AlX_3$—$LiAlH_4$ method for the hydrogenolysis of ketals involves the formation of aluminum trihydride, $AlH_3$, a hazardous compound. While, there are known alternatives to the hydrogenolysis processes, such processes suffer from the production of undesired byproducts and low yields. Furthermore, catalytic hydrogenolysis of acetals and ketals of organic hydrocarbons does not take place over most hydrogenation catalysts under normal hydrogenation conditions, even at relatively high temperatures and pressures.

One report in the literature describes the catalytic hydrogenolysis of certain ketals at moderate temperatures and pressures: Howard, W. L. and J. H. Brown, Jr., J. Org. Chem., 26, 1026 (1961). These authors noted that rhodium was the hydrogenolysis catalyst of choice, palladium much less desirable, while both platinum and ruthenium proved essentially inactive. The ketals studied by Howard and Brown were simple alkyl derivatives, and hence the products were simple ethers and alcohols, with the reaction occurring as shown below:

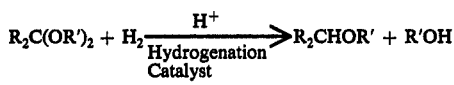

wherein the R groups were with one exception, $C_1$ to $C_4$ alkyl groups. Bronsted acids, such as hydrogen chloride, were used to provide the hydrogen ion. These processes required significant amounts of make-up acid.

SUMMARY OF THE INVENTION

An improved process for the hydrogenolysis of acetals and ketals of organic hydrocarbons results when the reaction takes place in the presence of a catalyst which consists essentially of a halide of a Group III A element and a supported platinum or rhodium hydrogenation catalyst. A combination of both supported catalysts may be present at the same time in accordance with this invention. The process is practiced at a temperature of from about −15° C. to about 125° C. and a pressure of from about 50 psia to about 2000 psia. The desired reaction products produced by the reaction are the same as produced by prior art processes hereinbefore discussed and are generally known to be ethers, alcohols, or hydroxy ethers, when a dioxolane structure is present in the acetal or ketal. Ethers are known to be useful as solvents, the alcohols have many well-known uses and the hydroxy ethers are useful as initiators for reaction with epoxides to form surfactants.

It is an object of this invention to provide an improved catalyst system for the hydrogenolysis of acetals and ketals of organic hydrocarbons.

It is an object of this invention to provide an improved process for the hydrogenolysis of acetals and ketals of organic hydrocarbons by providing a new catalyst for such processes whereby the reaction occurs at relatively low temperatures.

It is a further object of this invention to provide an improved hydrogenolysis reaction using an improved catalyst which does not necessitate the use of such dangerous compounds as lithium aluminumhydride or haloalkyl aluminum compounds.

DETAILED DESCRIPTION OF THE INVENTION

The acetals and ketals of organic hydrocarbons susceptible to reaction in the process of this invention may be defined by the general formula

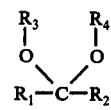

where $R_1$, $R_2$, $R_3$ and $R_4$ are organic hydrocarbon groups, particularly acyclic, alicyclic or aromatic hydrocarbon groups which may be substituted with other functional groups such as halide, hydroxyl, carbonyl, and the like, which do not interfere with the hydrogenolysis reaction. It is within the scope of this invention that $R_3$ and $R_4$ may be members of a common ring system resulting in a dioxolane structure. When an acetal is the feedstock, $R_1$ or $R_2$ is hydrogen.

In the usual practice of this invention, $R_1$ will be an alkyl hydrocarbon having from one to twenty carbon atoms; a cyclic compound, such as, for example, cyclohexane; or an aromatic compound, such as, for example, benzene, toluene, xylene, and the like. Normally, $R_2$ will be hydrogen or a lower alkyl group having one to four carbon atoms, and the like, but organic moities having a greater number of carbon atoms may also be present without adversely affecting the practice of the process of this invention. Usually, $R_3$ and $R_4$ will be alkyl groups having from one to about ten carbon atoms or be parts of a common ring structure such as a dioxolane, for example. With the latter, $R_3$ and $R_4$ together would be the hydrocarbon residue of ethylene glycol, 1,2-propyleneglycol, 2,3-butyleneglycol, and the like. Of course, any of the above organic groups may be substituted with functional groups which do not interfere with the attack on the C—O bond during the hydrogenolysis process.

The acetals and ketals of organic hydrocarbons are mixed and reacted with hydrogen, in the presence of the new catalyst system of this invention, under facile reaction conditions, to yield the corresponding alcohols, ethers, or ether-alcohols. The catalyst system of this invention consists essentially of, (1) a halide of an element from Group III A of the Periodic Table, and (2) a supported platinum or rhodium hydrogenation catalyst. Both of the latter could be present simultaneously in the practice of the process and such is preferred.

The first component is a halide of a Group III A Element. The Group III A elements useful in the practice of this invention are boron, aluminum, gallium, indium and thallium with boron and aluminum being especially preferred. The halogens, i.e., fluorine, chlorine, bromine, and iodine are useful in the practice of the invention with the most preferred halogens being fluorine and chlorine. Especially preferred for use as the first component of the improved catalyst system are boron trifluoride or aluminum trichloride. To improve the introduction of this component into the liquid phase system, the halide may be first mixed into an ether, such as a ethyl ether, to form liquid etherate, but such a step is optional.

The other component of the cocatalyst system especially useful in the practice of the invention are platinum and rhodium hydrogenation catalysts which are generally well known to those of ordinary skill in the art. Either, or both, of these supported hydrogenation catalyst are used in the catalyst system. Platinum on carbon hydrogenation catalyst wherein 5% platinum is present on a carbon support and rhodium on alumina, usually about 0.5 wt. % rhodium, are particularly preferred for use in the cocatalyst system of this invention. Of course, other well-known supports such as glass, silica, carborundum, zirconia, and the like are also useful as support materials for the platinum or rhodium hydrogenation catalyst. While the amount of the metal present on the support is not critical, such amount must be considered in adjusting the relative proportions of the two components of the cocatalyst system as discussed later. Of course, in addition to the aforementioned components, other materials may be used in conjunction therewith without departing from the scope of this invention.

The cocatalyst system which provides the improvement of this invention, is present in the liquid phase reaction in a catalytic amount for the hydrogenolysis to occur. Preferably, the catalyst system is present in amounts of from about 1 wt. % to about 20 wt. % based upon the weight of the acetal or ketal of the organic hydrocarbon charged to the reactor, and preferably from about 5 wt. % to about 18 wt. %. In determining the amount of catalyst system to be used, for simplicity, the supported hydrogenation catalyst will be considered to include the weight of the support itself thus making the operational determination of amounts more simple. Of course, where the supported catalyst has lesser or greater amounts of platinum or rhodium, as the case may be, the amount of catalyst system used will be easily adjusted within the aforesaid parameters. The weight of the Group III A halide will not include any material, such as diethyl ether, used to facilitate the introduction of the halide into the reaction mixture.

Within the catalyst system itself, from about 1 wt. % to about 50 wt. % is the halide of the Group III A element and, correspondingly, from about 99 wt. % to about 50 wt. % is the supported hydrogenation catalyst. The relative amounts of the active components of the catalyst system of this invention include the support to accomodate commercially available platinum and rhodium catalysts which may have varying amounts of platinum or rhodium and are easily adjusted within the foregoing parameters. The amounts of supported catalyst may include both platinum and rhodium catalyst in the same system. Of course, should other carriers and the like be incorporated into the catalyst system and introduced therewith into the reaction mixture, the foregoing percentages would be construed to establish the proportions of the active ingredients of the catalyst itself; i.e., the halide and the supported hydrogenation catalyst.

It is preferred, though not required, that the hydrogenolysis reaction occur in the presence of inert hydrocarbon solvents such as cyclohexane and the like. While other solvents, generally hydrocarbons, which are liquid at reaction conditions and not susceptible to appreciable hydrogenolysis can be used, the above-mentioned is preferable. The solvent, of course, aids in the conduct of the reaction but generally does not take part therein.

The use of the above-described catalyst system in the hydrogenolysis reaction of acetals and ketals of organic hydrocarbons makes it possible to operate such reaction at relatively facile conditions. The temperatures at which the hydrogenolysis reaction may be conducted range from about $-15°$ to about $125°$ C. with from about $0°$ to $70°$ C. being preferred. An especially preferred temperature range for the reaction is between about $10°$ and about $30°$ C. The reaction can be conducted at a pressure of from about 50 psia to about 2000 psia and preferably from about 900 psia to about 1200 psia to maintain the reaction system in the liquid phase.

Under the foregoing conditions, the time of the reaction will vary, of course. However, it has been found that under the preferred conditions, i.e., at around $0°$ to $70°$ C. and from about 900 psia to about 1200 psia the reaction occurs in from about 2 to about 3 hours. It is well-known that reaction rates will vary under different temperatures and pressures within the ranges at which this invention will be practiced and lesser or greater times may result at different conditions.

The foregoing improved process of this invention will be hereinafter more particularly described through the use of specific examples which are for the purposes of illustration and not limitation.

EXAMPLE 1

To a 300 ml. capacity stainless steel autoclave equipped with an electric heater and stirrer was charged a mixture of 100.0 gms of 2-hexyl-2-methyl-1,3-dioxolane and 9.5 gms of boron trifluoride etherate (formed by adding 1.5 gms $BF_3$ to 8.0 gms ethyl ether and mixing), with 4.0 gms of platinum (5 wt. %) on carbon supported hydrogenolysis catalyst and 4.0 gms of rhodium (0.5 wt. %) on alumina catalyst. After pressuring the autoclave to 1000 psig with hydrogen, the resulting mixture was heated at approximately 70° C. for 2.5 hours. Filtration of the crude reaction mixture resulted in a filtrate which, on the basis of NMR spectroscopy, infrared, and GLC analysis, contain the corresponding 2-(sec-octyloxy)ethanol, II, and bis(sec-octyl)ether of ethylene glycol, III showing that hydrogenating 2-hexyl-2-methyl-1,3 dioxolane in accordance with the instant inventive process yields II and III as follows:

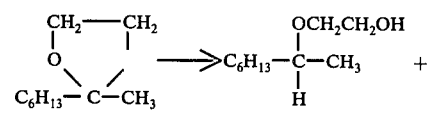

I           II

-continued

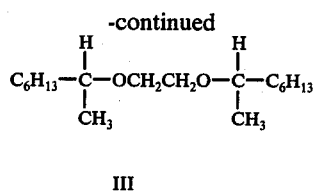

III

EXAMPLE 2

This example, using a prior art process for the hydrogenolysis of the same dioxolane compound as used in Example 1, was run to provide 2-(sec-octyloxy)ethanol, II, to use as a GLC standard to use when analyzing the compounds resulting from the practice of the improved process of this invention.

To a three-neck flask equipped with mechanical stirring, a thermometer, dropping funnel, water condenser, and nitrogen inlet was charged 60.5 gms anhydrous aluminum chloride and 130 cc. anhydrous diethyl ether. With ice-salt cooling, a slurry of lithium aluminum hydride (4.17 gms) in 125 cc diethyl ether was added. A solution of the dioxolane of Example 1 (37.8 gms) in 50 cc. diethyl ether, was added dropwise to the foregoing mixture in the three-neck flask under a nitrogen atmosphere at a rate such that reflux occurred. After completing the addition the mixture was refluxed for two hours at atmospheric pressure, then cooled. Additional water-saturated diethyl ether (100 ml) was added, followed by, first, 20 ml H$_2$O then 250 ml of 10 wt. % H$_2$SO$_4$, and finally 100 ml H$_2$O. The layers were separated, and the lower layer was extracted three times with diethyl ether. The extracts were then combined with the upper layer, washed with saturated NaHCO$_3$, dried over MgSO$_4$, filtered, and distilled. One material boiling at 92°–95° C. (1.7 mmHg) was shown to be the 2-(sec-octyloxy)ethanol, II, of Example 1 (NMR, and infrared analysis) to the extent of 34.8 gms, or a 91% yield. The reported boiling point was 99°–100° C. at 4 mm Hg pressure. This material was then employed as a GLC "standard" in experiments described below.

EXAMPLE 3

This example is within the scope of this invention and includes the isolation of bis(sec-octyl)ether of ethylene glycol, III, for use as a GLC standard. A mixture consisting of 70.0 gms. 2-hexyl-2-methyl-1,3 dioxolane, I, 5.2 gms boron trifluoride, 80 ml cyclohexane, 4.0 gms platinum (5 wt. %) on carbon and 4.0 gms of rhodium on alumina (0.5 wt. % Rh) was charged to a 300 ml stainless steel autoclave. After adding 80 ml of cyclohexane, the vessel was pressured to 950 psig with hydrogen with repressuring to 950 psig with hydrogen as required. The reaction was continued for 2.75 hours during which time the reaction temperature ranged from 15°–19° C. Filtration of the crude reaction mixture provided a homogeneous solution which, on the basis of GLC analysis, contained 10% unreacted starting material, 14% of the 2-(sec-octyloxy)ethanol, II, and 43% of a compound possessing a significantly longer retention time.

This unknown compound had a boiling point of approximately 130° C. at less than 0.3 mm Hg. On the basis of nuclear magnetic resonance, infrared spectral data and a molecular weight determination (wherein the molecular weight was calculated to be 322, and found to be 304), this material was assigned the alkoxy ether structure, III, shown below. This product served as a GLC "standard" in the described experiments.

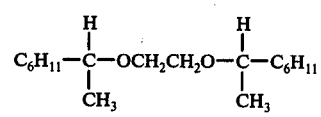

EXAMPLE 4

This Example demonstrates the improved process of this invention. A mixture of 90 gms 2-hexyl-2-methyl-1,3 dioxolane, 3.5 gms of 5 wt. % platinum on carbon supported catalyst, and 3.5 gms of rhodium (0.5 wt. %) on alumina supported catalyst were placed in a 300 ml capacity stainless steel autoclave. After adding a solution of 1.5 gms boron trifluoride in 8.0 gms. diethyl ether (boron trifluoride etherate), the reactor was pressured with hydrogen to 1000 psig. During a period of 2.0 hours, the autoclave was repressured to 1000 psig with hydrogen as required, while the reaction temperature was maintained at 14° C. Spectral analysis by NMR and IR established the presence of the desired alkyloxy alcohol, II, and the alkyloxy ether, III, in the crude reaction mixture. GLC analysis indicated the crude product consisted of unreacted dioxolane (24 wt. %), the alcohol, II, (23 wt. %) and the ether, III, (27 wt. %).

EXAMPLE 5

This Example illustrates the process of this invention when using one of the supported hydrogenation catalyst in the catalyst system. Repeating an experimental procedure as was used in the preceding example, 50.0 gms of dioxolane of Example 1, 3.0 gms of platinum (5 wt. %) on carbon supported catalyst, and boron trifluoride etherate was treated with hydrogen (1200 psig) at 0°–10° C for three hours. GLC analysis of the crude product established the presence of 44.7% by weight unreacted dioxolane, 20.9% alcohol, II, and 15.7% ether, III.

EXAMPLE 6

This Example shows that no hydrogenolysis occurs in absence of hydrogen in the presence of a catalyst system including a ruthenium on alumina catalyst. After charging a 300 ml capacity stainless steel autoclave pressure vessel with 50.0 gms of dioxolane, I, 9.6 gms of boron trifluoride etherate, 4.0 gms of 5% by weight platinum on carbon supported catalyst, and 4.0 gms of ruthenium on alumina supported catalysts, the mixture was allowed to stand over night at room temperature, then "stirred" at 6°–9° C. for three hours. Gas-liquid chromatography established the absence of alcohol, II, and ether, III, of Example 1 in the crude reactor effluent.

EXAMPLE 7

This Example shows that no reaction occurs if acetic acid is substituted for the halide of the catalyst of the invention. To a 300 ml stainless steel autoclave there was charged 20.0 gms 2-hexyl-2-methyl-1,3 dioxolane, I, 50 ml acetic acid, and 3.0 gms platinum (5 wt. %) on carbon supported catalyst. After pressuring the autoclave to 1200 psig with hydrogen, the contents of the pressure vessel were heated to 250° C. during a period of approximately 3.5 hours. Gas-liquid chromatography of the resulting material indicated the absence of both the alcohol, II, and the ether, III, products of Example 1.

EXAMPLE 8

This Example shows that no reaction occurs if a nickel hydrogenation catalyst is substituted for the supported hydrogenation catalyst of this invention. In the manner described in the preceding Example, a mixture of 50.0 gms of the dioxolane in Example 7, 3.0 gms boron trifluoride etherate, and 5.0 gms of a nickel hydrogenation catalyst were placed in a 300 ml autoclave, pressured to 1300 psig with hydrogen, and stirred at 14°-15° C. for 2.0 hours. Analysis of the crude reaction mixture by GLC techniques indicated that neither the alcohol, II, nor the ether, III, of Example 1 were formed.

EXAMPLE 9

This Example shows that no reaction occurs when a supported ruthenium hydrogenation catalyst is substituted for the supported catalyst of this invention. In the manner described in Example 1, 50.0 gms of the dioxolane of Example 1 and 2.0 gms of boron trifluoride etherate mixed and reacted under 1200 psig hydrogen in the presence 3.0 gms of ruthenium on alumina supported hydrogenation catalyst at 28°-30° C. for approximately 2.5 hours. On the basis of GLC analysis of the crude reaction mixture, neither the alcohol, II, nor the ether, III, of Example 1 were products of this reaction.

EXAMPLE 10

This Example shows the use of $AlCl_3$ as the cocatalyst in the practice of the invention. To a mixture, in a 300 ml stainless steel autoclave, of 50.0 mls of the dioxolane used in previous examples, 3.0 gms of the platinum (5 wt. %) on carbon, and 3.0 gms of the rhodium (0.5 wt. %) on alumina supported catalysts, there was added approximately 0.2 gms of anhydrous aluminum trichloride. The resulting material was stirred under 1200 psig hydrogen for 2.0 hours at 13°-15° C. Gas-liquid chromatography established the presence of both the alcohol, II, and the ether, III, of Example 1.

EXAMPLE 11

This Example shows that no reaction occurs in the absence of hydrogen even in the presence of $AlCl_3$. Stirring a mixture of 20.0 ml of the dioxolane of Example 1 as used in previous examples in approximately 0.5 gms aluminum chloride at room temperature and atmospheric pressure gave a turbid liquid which, on the basis of gas-liquid chromatography, did not contain either the alcohol, II, or the ether, III.

EXAMPLE 12

This Example shows that no reaction occurs when tin tetrachloride is substituted for the halide in the catalyst system of this invention. Subjecting a mixture of 50.0 gms of the dioxolane used in Example 1, 2.0 gms of tin tetrachloride, 4.0 gms of platinum (5 wt. %) on carbon supported catalysts, 4.0 gms. of rhodium (0.5 wt. %) on alumina support catalyst, and 10 mls of cyclohexane in a 300 ml stainless steel autoclave subjected to 1100 psig of hydrogen pressure at temperatures up to 74° C. over a period of 3 hours did not result in the formation of either the desired alcohol, II, or the ether, III, based upon GLC analysis of the reactor contents.

EXAMPLE 13

This Example shows that no reaction occurs when zinc chloride is substituted for the halide in the cocatalyst of the invention. Using identical procedures and reaction conditions as those of Example 12, zinc chloride was substituted for tin tetrachloride, and gave the same results. Neither the alcohol, II, nor the ether, III, products of Example 1 were detected by gas-liquid chromatography.

EXAMPLE 14

This Example shows that no reaction occurs when HCl is substituted for the halide, even in the presence of several hydrogenolysis catalyst. Fifty grams of the dioxolane of Example 1, a small amount of HCl, and 1 gm each of supported rhenium, rhodium, ruthenium, platinum, and palladium were subjected to approximately 1200 psig hydrogen for 2.0 hours at 12°-14° C. Gas-liquid chromatographic data established the absence of both the alcohol, II, and the ether, III.

Table I, summarizes the results of Examples 1 through 14 to demonstrate the surprising results achieved using the catalyst system of this invention at the reaction conditions of the improved process of this invention as compared with other catalysts which might appear to be equally appropriate. The following example demonstrates the general applicability of the improved process of this invention to the hydrogenolysis of an acetal of an organic hydrocarbon.

TABLE I

| Example | $H_2$ present | Temperature °C | Pressure, psig | Time, hrs. | Bronsted Acid | Hydrogenation Catalyst | Cocatalyst | Products (II), (III) present? | Unreacted charge, wt. percent |
|---|---|---|---|---|---|---|---|---|---|
| 1 | Yes | 70 | 1000 | 2.5 | | (1) and (2) | $BF_3$ | Yes | — |
| 2 | Yes | 15-20° C | 0 | 2.0 | | — | $AlCl_3$* | III | — |
| 3 | Yes | 15-19° C | 950 | 2.75 | | (1) and (2) | $BF_3$ | Yes | 10% |
| 4 | Yes | 14° C | 1000 | 2.0 | | (1) and (2) | — | Yes | — |
| 5 | Yes | 0-10° C | 1200 | 2.0 | | (1) | $BF_3$ | Yes | 44.7% |
| 6 | No | (1) approx 18° C (2) 6-9° C | 0 | (1) 6.0+ (2) 3.0 | | (1), Ru on Alumina | $BF_3$ | No | −100.0% |
| 7 | Yes | 250° C | 1200 | 3.5 | Acetic Acid | (1) | — | No | −100.0% |
| 8 | Yes | 14-15° C | 1300 | 2.0 | | NIckel | $BF_3$ | NO | −100.0% |
| 9 | Yes | 28-30° C | 1200 | 2.25 | | Ru on Alumina | $BF_3$ | NO | −100.0% |
| 10 | Yes | 13-15° C | 1200 | 2.0 | | (1) and (2) | $AlCl_3$ | Yes | — |
| 11 | No | approx 18° C | 0 | 1.0 | | — | $AlCl_3$ | No | −100.0% |
| 12 | Yes | 0° C to 74° C | 1100 | 3.0 | | (1) and (2) | $SnCl_4$ | No | −100.0% |
| 13 | Yes | 0° C to 74° C | 1100 | 3.0 | | (1) and (2) | $ZnCl_2$ | No | −100.0% |

TABLE I-continued

| Example | H₂ present | Temperature °C | Pressure, psig | Time, hrs. | Bronsted Acid | Hydrogenation Catalyst | Cocatalyst | Products (II), (III) present? | Unreacted charge, wt. percent |
|---|---|---|---|---|---|---|---|---|---|
| 14 | Yes | 12–14° C | 1200 | 2.0 | HCl | (1) and (2)** | — | No | −100.0% |

(1) Platinum on Carbon
(2) Rhodium on Alumina
*also LiAlH₄
**also rhenium, ruthenium, and palladium

EXAMPLE 15

To a 300 ml stainless steel autoclave was added a mixture of heptyldioxolane (100 gms), 12.0 gms of boron trifluoride etherate and 5.0 gms of a platinum (1.0 wt. %) on carbon hydrogenation catalyst. The autoclave was pressured to 1200 psig with hydrogen at room temperature and stirred at 31°–33° C. for two hours. During this period of time the hydrogen pressure dropped indicating that the hydrogenolysis reaction as in Example 1 was occurring.

The preceeding examples can be repeated with similar success by substituting other generically and specifically described acetals and ketals for those employed in the examples. As will be evident to those skilled in the art, various modifications of this invention can be made in the light of the discussion and disclosure herein set forth without departing from the spirit or scope thereof.

I claim as my invention:

1. In a liquid phase process for the hydrogenolysis of dioxolanes to produce the corresponding ethers, alcohols, or hydroxy ethers, in the presence of a catalyst, the improvement which comprises:
    mixing and reacting the said dioxolane with hydrogen at a temperature within the range of from about −15° C. to about 125° C. and a pressure of from about 50 psia to about 2000 psia in the presence of a catalytic amount of a catalyst consisting essentially of:
    (1) a halide of a Group III A element, and
    (2) a supported platinum or rhodium hydrogenation catalyst, and wherein the said dioxolane has the formula:

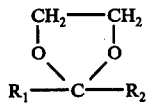

wherein R₁ is selected from the group consisting of alkyl of from 1 to 20 carbon atoms, cyclohexyl, phenyl, tolyl and xylyl and R₂ is selected from the group consisting of hydrogen and alkyl of from 1 to 4 carbon atoms.

2. The process of claim 1, wherein the temperature is from about 0° to about 70° C. and the pressure is from about 900 psia to about 1200 psia.

3. The process of claim 1, wherein the halide is aluminum trichloride or boron trifluoride.

4. The process of claim 3, wherein the halide is boron trifluoride.

5. The process of claim 1, wherein the supported hydrogenation catalyst is platinum on carbon.

6. The process of claim 1, wherein the supported hydrogenation catalyst is rhodium on alumina.

7. The process of claim 1 wherein the supported hydrogenation catalyst includes both platinum on carbon and rhodium on alumina.

8. In a liquid phase process for the hydrogenolysis of dioxolanes to produce the corresponding ethers, alcohols, or hydroxy ethers, in the presence of a catalyst, the improvement which comprises:
    mixing and reacting the dioxolane with hydrogen at a temperature within the range of from about −15° C. to about 125° C. and a pressure of from about 50 psia to about 2000 psia in the presence of from about 1 wt. % to about 20 wt. %, based upon the weight of the dioxolane charged to the reactor, of a catalyst consisting essentially of:
    (1) from about 1 wt. % to about 50 wt. % of a halide of a Group III A element, and
    (2) correspondingly, from about 50 wt. % to about 99 wt. % of a supported platinum or rhodium hydrogenation catalyst or combination thereof, and wherein the said dioxolane has the formula:

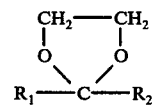

wherein R₁ is selected from the group consisting of alkyl of from 1 to 20 carbon atoms, cyclohexyl, phenyl, tolyl and xylyl and R₂ is selected from the group consisting of hydrogen and alkyl of from 1 to 4 carbon atoms.

9. The process of claim 8 wherein the catalyst is present in an amount of from about 5 wt. % to about 18 wt. %, based upon the weight of the dioxolane charged and the mixing and reacting step occurs at a pressure of from about 900 psia to about 1200 psia and a temperature of from about 0° to about 70° C.

10. The process of claim 1 wherein the said dioxolane is 2-hexyl-2-methyl-1,3 dioxolane.

11. The process of claim 1 wherein the said catalyst is boron trifluoride and a supported rhodium hydrogenation catalyst.

12. The process of claim 1 wherein the said catalyst is boron trifluoride and a supported platinum hydrogenation catalyst.

13. The process of claim 8 wherein the said dioxolane is 2-hexyl-2-methyl-1,3 dioxolane.

* * * * *